(12) United States Patent
Sato

(10) Patent No.: US 8,309,138 B2
(45) Date of Patent: Nov. 13, 2012

(54) PHARMACEUTICAL COMPOSITION COMPRISING MICROPARTICLE OILY SUSPENSION

(75) Inventor: Yasunori Sato, Kanagawa (JP)

(73) Assignee: ASKA Pharmaceutical Co., Ltd., Tokyo (JP)

(*) Notice: Subject to any disclaimer, the term of this patent is extended or adjusted under 35 U.S.C. 154(b) by 272 days.

(21) Appl. No.: 12/526,825

(22) PCT Filed: Feb. 15, 2008

(86) PCT No.: PCT/JP2008/000230
§ 371 (c)(1),
(2), (4) Date: Dec. 29, 2009

(87) PCT Pub. No.: WO2008/099615
PCT Pub. Date: Aug. 21, 2008

(65) Prior Publication Data
US 2010/0092565 A1  Apr. 15, 2010

(30) Foreign Application Priority Data
Feb. 16, 2007  (JP) ................. 2007-035916

(51) Int. Cl.
*A61K 9/14* (2006.01)
*A61K 31/506* (2006.01)
(52) U.S. Cl. ............. 424/498; 424/502; 514/256
(58) Field of Classification Search .......... None
See application file for complete search history.

(56) References Cited

U.S. PATENT DOCUMENTS

| | | | |
|---|---|---|---|
| 5,686,455 A | 11/1997 | Adams et al. | |
| 5,985,902 A | 11/1999 | Talley et al. | |
| 6,511,997 B1 | 1/2003 | Minami et al. | |
| 7,101,899 B1 | 9/2006 | Ohkawa et al. | |
| 7,321,040 B2 | 1/2008 | Braganza et al. | |
| 7,423,047 B2 | 9/2008 | Brookings et al. | |
| 2003/0166709 A1 | 9/2003 | Rimpler et al. | |
| 2003/0181411 A1 | 9/2003 | Bosch et al. | |
| 2004/0009225 A1 | 1/2004 | Vanderbist et al. | |
| 2006/0128759 A1 | 6/2006 | Laufer et al. | |
| 2007/0104742 A1 | 5/2007 | Lehtola et al. | |

FOREIGN PATENT DOCUMENTS

| | | |
|---|---|---|
| EP | 1832584 | 9/2007 |
| JP | 6-016556 | 1/1994 |
| JP | 6-501003 | 2/1994 |
| JP | 7-138151 | 5/1995 |
| JP | 10-081621 | 3/1998 |
| JP | 11-506432 | 6/1999 |
| JP | 11-506433 | 6/1999 |
| JP | 11-302156 | 11/1999 |
| JP | 2000-086657 | 3/2000 |
| JP | 2000-516244 | 12/2000 |
| JP | 2001-505910 | 5/2001 |
| JP | 2002-502812 | 1/2002 |
| JP | 2005-112753 | 4/2002 |
| JP | 2002-537337 | 11/2002 |
| JP | 2003-510348 | 3/2003 |
| JP | 2004-503493 | 2/2004 |
| JP | 2004-099442 | 4/2004 |
| JP | 2005-516943 | 6/2005 |
| JP | 2006-513267 | 4/2006 |
| JP | 2007-039408 | 2/2007 |
| WO | 92/04893 | 4/1992 |
| WO | 93/14081 | 7/1993 |
| WO | 96/25405 | 8/1996 |
| WO | 96/36321 | 11/1996 |
| WO | 96/36338 | 11/1996 |
| WO | 98/07414 | 2/1998 |
| WO | 98/25621 | 6/1998 |
| WO | 98/52940 | 11/1998 |
| WO | 99/39699 | 8/1999 |
| WO | 00/25772 | 5/2000 |
| WO | 00/38652 | 7/2000 |
| WO | 00/39116 | 7/2000 |
| WO | 00/40220 | 7/2000 |
| WO | 00/50038 | 8/2000 |
| WO | 00/64894 | 11/2000 |
| WO | 01/24780 | 4/2001 |
| WO | 01/95886 | 12/2001 |
| WO | 02/15903 | 2/2002 |
| WO | 02/24172 | 3/2002 |
| WO | 03/053403 | 7/2003 |
| WO | 2004/000846 | 12/2003 |
| WO | 2004/014907 | 2/2004 |
| WO | 2004/017968 | 3/2004 |
| WO | 2004/022555 | 3/2004 |

(Continued)

OTHER PUBLICATIONS

Gallagher et al., "Regulation of Stress-Induced Cytokine Production by Pyridinylimidazoles; Inhibition of CSBP Kinase" *Bioorganic & Medicinal Chemistry*, vol. 5, No. 1, pp. 49-64, 1997.

Lamprecht et al., "Size-Dependent Bioadhesion of Micro- and Nanoparticulate Carriers to the Inflamed Colonic Mucosa" *Pharmaceutical Research*, vol. 18, No. 6, pp. 788-793, 2001.

Yamamoto et al., "Ryushi Bussei Seigyo ni yoru Biryushi Drug Delivery System no Kino Sekkei", *Drug Delivery System*, vol. 17-4, pp. 321-329, along with a partial English translation, 2002.

International Search Report that issued with respect to PCT/JP2008/000230, mailed Apr. 1, 2008.

International Preliminary Report on Patentability that issued with respect to PCT/JP2008/000230, mailed Aug. 27, 2009.

Japanese Office Action that issued with respect to patent family member Japanese Patent Application No. 2008-558013, dated Jul. 7, 2009.

(Continued)

*Primary Examiner* — Susan Tran
*Assistant Examiner* — Jessica Worsham
(74) *Attorney, Agent, or Firm* — Greenblum & Bernstein, P.L.C.

(57) ABSTRACT

A pharmaceutical composition comprising a suspension of medicinally-active ingredient microparticles having a mean particle diameter of 20 μm or smaller in a base oil which can achieve extremely high intestinal absorption and bioavailability especially when the medicinally-active ingredient is hardly water-soluble.

6 Claims, 1 Drawing Sheet

FOREIGN PATENT DOCUMENTS

| | | |
|---|---|---|
| WO | 2004/058286 | 7/2004 |
| WO | 2004/072072 | 8/2004 |
| WO | 2004/073628 | 9/2004 |
| WO | 2004-073692 | 9/2004 |
| WO | 2005/013938 | 2/2005 |
| WO | 2005/073189 | 8/2005 |
| WO | 2005/085249 | 9/2005 |
| WO | 2005/105052 | 11/2005 |
| WO | 2006/070927 | 7/2006 |

OTHER PUBLICATIONS

Extended European Search Report that issued with respect to patent family member EP App. No. 08710384.2, dated May 4, 2010.
Australian Office Action issued with respect to counterpart Australian application No. 2008215659, dated Jun. 27, 2012.

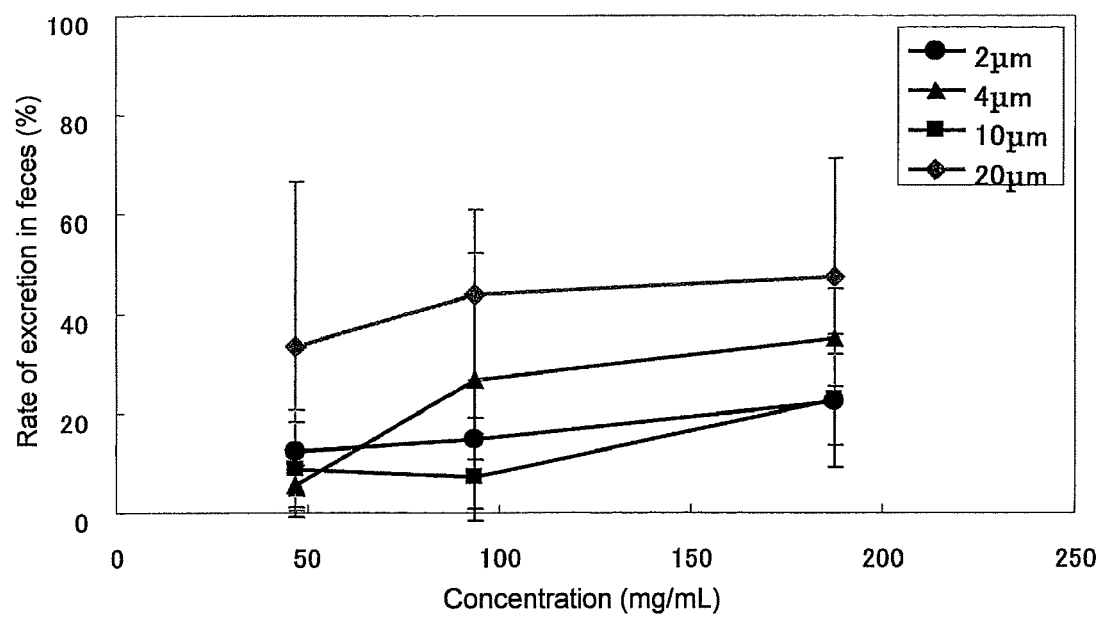

PHARMACEUTICAL COMPOSITION COMPRISING MICROPARTICLE OILY SUSPENSION

TECHNICAL FIELD

The present invention relates to a pharmaceutical composition comprising a suspension of microparticles of a medicinally-active ingredient in a base oil which can achieve high bioavailability.

BACKGROUND ART

For improvement of bioavailability of an active ingredient of a pharmaceutical product and the like, various pharmaceutical contrivances have been made so far. For example, Japanese Patent Unexamined Publication (KOKAI) No. 2004-99442 describes a method of preparing microparticles of a hardly soluble drug substance having a mean particle diameter of several hundreds nanometers by dry grinding of a mixture of the hardly soluble drug substance, polyvinylpyrrolidone, and sodium dodecylsulfate. However, in order to prepare microparticles having a mean particle diameter of several hundreds nanometers, a special grinder or grinding process may be required, and moreover, microparticles of the aforementioned level have drawbacks in handling, for example, they are hardly wetted with water, and they coagulate in an aqueous medium. Further, the aforementioned publication fails to disclose an oily suspension of an active ingredient.

Japanese Patent Unexamined Publication No. 2005-112753 describes that, as for a soft capsule in which an active ingredient is suspended in an oil or a fat, bioavailability can be improved by further adding a hydrogenated oil or a fat to the content. However, this publication is totally silent about correlation of mean particle diameter of the active ingredient and bioavailability thereof in the oily suspension preparations.

Japanese Patent Unexamined Publication No. 7-138151 discloses a soft capsule containing 5 to 40 mass % of a powdered raw material that is hardly soluble in an oil and 60 to 95 mass % of an oil-soluble raw material. The aforementioned publication describes values of 0.1 nm to 1 mm as a mean particle diameter of the hardly oil-soluble powdered raw material in paragraph [0008]. The pharmaceutical preparation disclosed in the publication is explained to achieve simultaneous high-dose intake of the hardly oil-soluble powdered raw material and the oil-soluble raw material, however, a purpose of providing the preparation is not improvement in bioavailability of an active ingredient. Further, this publication is completely silent about correlation between a mean particle diameter of an active ingredient and bioavailability thereof.

International Publication WO2004/073692 describes in page 3, lines 29 to 39 that "there are recently marketed gelatin soft capsules containing about 15 mass % of ciclosporin as an immunosuppressant, a solubilizer, and a surfactant and having increased water solubility, no deposition in the gastrointestinal tract after oral administration, little fluctuation in oral absorption, and improved oral absorption (Neoral (registered trademark), Clin. Transplantation, Vol. 10, 364-373 (1996)), and sustained-release hard capsules encapsulating a semi-solid oily suspension matrix formed by simply suspending captopril in fat and oil (International Journal of Pharmaceutics, Vol. 41, 245-254 (1988))". However, Neoral is a microemulsion preparation of which particle diameter is not larger than 0.15 µm, and is not an oily suspension of an active ingredient prepared as microparticles, and the aforementioned captopril hard capsules aim at sustained release, in which the active ingredient is not made into microparticles.

Further, Japanese Patent Unexamined Publication Nos. 10-81621, 11-302156, Japanese Patent Unexamined Publication based on PCT Application (KOHYO) Nos. 2000-516244, 2006-513267, and Japanese Patent Unexamined Republication based on PCT Application (SAIKOHYO) No. 2005-13938 describe a suspension of hardly water-soluble compounds made into microparticles. However, these publications do not include any specific description or examples concerning a process of suspending the hardly water-soluble compounds made into microparticles. Therefore, the aforementioned description of the term "suspension" in these publications is a mere general explanation, and is not described so as to be enabled.

Furthermore, Japanese Patent Unexamined Publication Nos. 6-16556, 2004-99442 and Japanese Patent Unexamined Publication based on PCT Application No. 2005-516943 include descriptions concerning aqueous suspensions of hardly water-soluble compounds made into microparticles. However, these publications neither suggest nor teach improvement of bioavailability by providing an oily suspension.

Japanese Patent Unexamined Publication based on PCT Application No. 2002-528492 discloses that bioavailability of isotretinoin, which is used for treatment of resistant cystic acne, is improved by subjecting an oily suspension of isotretinoin, per se, having a mean particle diameter of about 90 to 100 µm to a microparticle forming operation to obtain a mean particle diameter of 5 to 30 µm. Further, Japanese Patent Unexamined Publication No. 2007-039408 describes a method of preparing microparticle creatine having a mean particle diameter of 2 µm or smaller by dispersing creatine in a non-aqueous solvent (ethanol) and then performing grinding in a bead mill. However, although these two publications teach that bioavailability is improved by making particle diameter smaller, they do not suggest nor teach that, by making a drug substance into microparticles and forming an oily suspension of the microparticles, higher bioavailability can be achieved compared with that obtainable by simply making the drug substance into microparticles.

IBD (Inflammatory Bowel Disease) is a general term referring to Crohn's disease and ulcerative colitis, and both of the two diseases are intractable diseases which recurs and abates repeatedly. Since acceleration of immune functions and increase of inflammatory cytokines such as tumor necrosis factor-α (TNF-α) and an interleukin-1 (IL-1) are observed in pathological conditions of IBD, inhibition of the p38MAP kinase, which locates upstream of these inflammatory cytokines or the inflammatory reaction pathways thereof, is expected to be effective for therapeutic treatment of IBD (see, for example, J. Pharmacol. Exp. Ther., 284, 687-692 (1998); N. Engl. J. Med., 337, 1029-1035 (1997); Gut., 40, 628-633 (1997)).

As compounds having a p38MAP kinase inhibitory action, there are so far known, for example, imidazole derivatives (see, Bioorganic & Medicinal Chemistry, Vol. 5, No. 1, 49-64 (1997), WO93/14081), pyrazole derivatives (see, WO98/52940, WO00/39116), isoxazole derivatives (see, Japanese Patent Unexamined Publication No. 2000-86657, WO96/25405, WO2004/17968, WO2004/22555, WO2006/070927), thiazole derivatives (see, WO00/64894), triazolopyridine derivatives (see WO2004/72072), pyridopyrimidine derivatives (see, WO2004/14907), naphthylidine derivatives (see, WO2004/73628), 6-membered condensed pyrazole derivatives (see, WO2005/73189, WO2005/85249), bicyclic hetero aromatic ring compound (see, WO2004/00846), and the like.

However, no p38MAP kinase inhibitor as a pharmaceutical product has yet been launched into the market.

From a viewpoint of the mechanism of action, p38MAP kinase inhibitors has been developed mainly for systemic inflammatory diseases such as rheumatism as indications thereof. However, p38MAP kinase inhibitors have many problems such as distribution into the central nervous system, hepatotoxicity, and nephrotoxicity, and therefore, the inhibitor was found to be difficult to be developed as a pharmaceutical product for treatments of the diseases by maintaining a constant blood level. However, p38MAP kinase inhibitors may possibly be suitable for local inflammatory diseases such as IBD, and therefore, development of therapeutic agent for IBD is expected which acts locally such as in the intestinal tract.

DISCLOSURE OF THE INVENTION

An object of the present invention is to provide a pharmaceutical product which has increased bioavailability of an active ingredient. In particular, the major objects of the present invention are to provide a means for improving bioavailability of a hardly water-soluble active ingredient by increasing absorption from the intestinal tract, and by applying the aforementioned means, to provide a pharmaceutical product having increased bioavailability of a hardly water-soluble active ingredient.

Many of drug substances are excreted, for the most part, in feces as unchanged form after oral administration in an ordinary manner. Especially when a drug substances is hardly water-soluble, the drug substances most likely exhibits such tendency. A rate of excretion in feces can be reduced (in other words, bioavailability is increased) when drug substances are made into microparticles. However, it is common technical knowledge of those skilled in the art that there is also a limit in the decrease of the rate of excretion into feces which is achieved by making drug substances into microparticles.

The inventors of the present invention conducted various researches to achieve the aforementioned object, and found that when an active ingredient was made into microparticles, and an oily suspension thereof was formed, the active ingredient was successfully allowed to be present on the intestinal wall and intestinal tract tissues, thereby a rate of excretion in feces was significantly reduced and bioavailability thereof was markedly increased. They also found that the decrease of the rate of excretion in feces correlated with a mean particle diameter of the active ingredient. The present invention was accomplished on the basis of these findings.

The present invention thus provides a pharmaceutical composition comprising a suspension of microparticles of a medicinally-active ingredient in a base oil, wherein said microparticles have a mean particle diameter of 20 μm or smaller.

According to a preferred embodiment of the present invention, there is provided the aforementioned pharmaceutical composition, wherein the medicinally-active ingredient is a hardly water-soluble medicinally-active ingredient, and according to another preferred embodiment, there is provided the aforementioned pharmaceutical composition, wherein the medicinally-active ingredient is a medicinally-active ingredient for prophylactic and/or therapeutic treatment of an inflammatory bowel disease. Furthermore, according to other preferred embodiments of the present invention, there are provided the aforementioned pharmaceutical composition, wherein the medicinally-active ingredient is a compound or a physiologically acceptable salt thereof having a p38MAP kinase inhibitory action; the aforementioned pharmaceutical composition, wherein the microparticles of the medicinally-active ingredient have a mean particle diameter of 10 μm or smaller; and the aforementioned pharmaceutical composition, which is for oral administration, and is used for prophylactic and/or therapeutic treatment of an inflammatory bowel disease.

According to other preferred embodiments of the present invention, there are provided the aforementioned pharmaceutical composition, wherein the suspension contains one kind or two or more kinds of pharmaceutical additives selected from the group consisting of a suspending agent, a wax, and a dispersing agent; the aforementioned pharmaceutical composition, which contains each of the pharmaceutical additives in an amount in the range of 0.1 to 10 mass % based on the total mass of the suspension; the aforementioned pharmaceutical composition, which contains the medicinally-active ingredient in an amount of within the range of 1 to 30 mass % based on the total mass of the suspension; the aforementioned pharmaceutical composition, which contains the base oil in an amount of within the range of 70 to 99 mass % based on the total mass of the suspension; and the aforementioned pharmaceutical composition, which is in the form of a soft capsule filled with said suspension.

From other aspects of the present invention, there are provided a method for preparing the aforementioned pharmaceutical composition, which comprises the step of suspending the microparticles of the medicinally-active ingredient having a mean particle diameter of 20 μm or smaller in a base oil; and any of the aforementioned pharmaceutical compositions, which is obtainable by the aforementioned method.

The pharmaceutical composition of the present invention has increased absorption of a medicinally-active ingredient from the intestinal tract and remarkably improved bioavailability. In particular, said composition is characterized to achieve extremely high intestinal absorption and bioavailability also when the medicinally-active ingredient is hardly water-soluble.

BRIEF DESCRIPTION OF THE DRAWING

FIG. 1 A graph depicting influences of a mean particle diameter and a concentration of a medicinally-active ingredient on the rate of excretion in feces (Example 19).

BEST MODE FOR CARRYING OUT THE INVENTION

Type of the medicinally-active ingredient which can be used for the pharmaceutical composition of the present invention is not particularly limited. Where a hardly water-soluble medicinally-active ingredient is provided as the pharmaceutical composition of the present invention, bioavailability can be markedly increased. Accordingly, a medicinally-active ingredient having the aforementioned property is preferably used in the pharmaceutical composition of the present invention. Examples of the hardly water-soluble property include, for example, the solubility defined in the Japanese Pharmacopoeia as "hardly soluble" or solubility lower than said definition (solubility of a compound in water as being 10 mg/mL or less). A medicinally-active ingredient can be preferably used in the present invention which has, among the aforementioned hardly soluble properties, a solubility falling within the definition in the Japanese Pharmacopoeia as "substantially insoluble" (i.e., solubility of a compound in water as being 0.1 mg/mL or less: this property is referred to as "hardly water-soluble" in the specification).

A pharmacological action possessed by the medicinally-active ingredient used in the pharmaceutical composition of the present invention and a disease as a target for application of the pharmaceutical composition of the present invention are not particularly limited. According to the pharmaceutical composition of the present invention, a substantial ratio of a medicinally-active ingredient can be delivered and maintained in the intestinal tract, even if the active ingredient is hardly water-soluble, and therefore the pharmaceutical composition of the present invention can be preferably used for prophylactic and/or therapeutic treatment of digestive organ-related diseases. Further, examples of the medicinally-active ingredient used in the pharmaceutical composition of the present invention include, for example, medicinally-active ingredients for use in prophylactic and/or therapeutic treatment of digestive organ-related diseases, preferably inflammatory bowel diseases. By orally administering the aforementioned medicinally-active ingredient as the pharmaceutical composition of the present invention, the active ingredient is localized or retained in the intestinal tract wall or in the intestinal tract tissues, thereby pharmacological action of said active ingredient is exhibited in the intestinal tract.

Examples of the medicinally-active ingredient for use in prophylactic and/or therapeutic treatment of inflammatory bowel diseases include, for example, compounds and salts thereof having a p38MAP kinase inhibitory action, steroid compounds and salts thereof, antibodies directed to inflammatory cytokines, compounds and salts thereof having an immunosuppressive action, and the like. Among them, the compounds and salts thereof having a p38MAP kinase inhibitory action are preferred, and specific examples of such compounds or salts thereof include, for example, various compounds described in the publications mentioned above. Even if those compounds or salts thereof are hardly water-soluble, these compounds can be preferably used in the pharmaceutical composition of the present invention.

Examples of the compounds and salts thereof having a p38MAP kinase inhibitory action include, for example, the compounds represented by the following general formula (I):

[Formula 1]

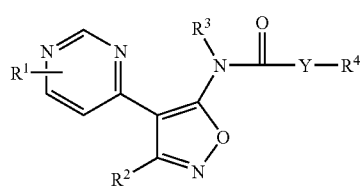

(I)

wherein $R^1$ represents hydrogen atom, a lower alkyl group, amino group, a lower alkylamino group, a di(lower alkyl) amino group, a phenyl(lower alkyl)amino group, an acylamino group, a halogen atom, a lower alkoxyl group, a lower alkylthio group, or a lower alkylsulfinyl group; $R^2$ represents an unsubstituted aryl group, an unsubstituted heteroaryl group, or an aryl group or heteroaryl group substituted with 1 to 3 substituents selected from the group consisting of a halogen atom, a lower alkyl group, a lower alkoxyl group, a lower haloalkyl group, a lower alkylenedioxy group and benzyloxy group; $R^3$ represents hydrogen atom, or a lower alkyl group; $R^4$ represents a substituted or unsubstituted phenyl group, or a substituted or unsubstituted heterocyclic group; Y represents a group of —$(CH_2)_n$—, —CO—, —CH($CH_3$)—, —O—, —NH—, —C($CH_3$)$_2$—, or —C(—$CH_2CH_2$—)—; and n is an integer of 0 to 3, and salts thereof disclosed in International Publication WO2006/070927. Definitions of the substituents and the like mentioned in the aforementioned formula are explained in International Publication WO2006/070927, and accordingly, entire disclose of the aforementioned International Publication is incorporated in the disclosure of the specification by reference.

Preferred examples of the compounds of the aforementioned general formula (I) and salts thereof include, for example:
5-[(2-chlorophenyl)acetylamino]-3-(4-fluorophenyl)-4-(4-pyrimidinyl)isoxazole,
5-[(2-chloro-6-fluorophenyl)acetylamino]-3-(4-fluorophenyl)-4-(4-pyrimidinyl)isoxazole,
3-(4-chlorophenyl)-5-[(2-chlorophenyl)acetylamino]-4-(4-pyrimidinyl)isoxazole,
5-[(2-chlorophenyl)acetylamino]-3-(2,4-difluorophenyl)-4-(4-pyrimidinyl)isoxazole,
3-(2,4-difluorophenyl)-5-[(3-methylphenyl)acetylamino]-4-(4-pyrimidinyl)isoxazole,
5-[(2-chlorophenyl)acetylamino]-3-(2-fluoro-4-methoxyphenyl)-4-(4-pyrimidinyl)isoxazole,
5-[(2-chlorophenyl)acetylamino]-3-(2,3-methylenedioxyphenyl)-4-(4-pyrimidinyl)isoxazole,
5-[(2-chlorophenyl)acetylamino]-3-(3-methylphenyl)-4-(4-pyrimidinyl)isoxazole,
5-[(2-bromophenyl)acetylamino]-3-(3-methylphenyl)-4-(4-pyrimidinyl)isoxazole,
3-(3-methylphenyl)-5-[(2-methylphenyl)acetylamino]-4-(4-pyrimidinyl)isoxazole,
3-(3-methylphenyl)-5-[(3-methylphenyl)acetylamino]-4-(4-pyrimidinyl)isoxazole,
3-(2-fluoro-5-methylphenyl)-5-(phenylacetylamino)-4-(4-pyrimidinyl)isoxazole,
5-[(3-methoxyphenyl)acetylamino]-3-(3-methyl-4-fluorophenyl)-4-(4-pyrimidinyl)isoxazole,
3-(3-methyl-4-fluorophenyl)-5-[(2-methylphenyl)acetylamino]-4-(4-pyrimidinyl)isoxazole,
and salts thereof. However, the compounds are not limited to these examples.

The microparticles of the medicinally-active ingredient contained in the pharmaceutical composition of the present invention are microparticles having a mean particle diameter of 20 μm or smaller, and they are preferably microparticles having a mean particle diameter of 10 μm or smaller. A lower limit of the mean particle diameter of the microparticles is not particularly limited. For example, 0.5 μm or larger, preferably 1 μm or larger.

In the specification, the "mean particle diameter" is meant as a median diameter which is a particle diameter representing a 50% cumulative value in an cumulative distribution curve. Methods for measuring a mean particle diameter are well-known and ordinary used methods for those skilled in the art. A particle diameter distribution curve of a medicinally-active ingredient contained in the pharmaceutical composition of the present invention may be a multi-peak particle diameter distribution curve as well as a single-peak particle diameter distribution curve. The curve may be a particle diameter distribution curve in which two or more peaks are partially overlapped. When the particle diameter distribution curve includes multiple peaks, relative size of each peak is not particularly limited. A shape of a peak in a particle diameter distribution curve is not particularly limited, and may be a shape of steep mountain or a peak containing a broad trapezoid. When a particle diameter distribution curve includes multiple peaks, the maximum particle diameter in a peak, that corresponds to the minimum particle diameter, may be, for example, about 50 μm or smaller, preferably 40 μm or smaller, still more preferably 30 μm or smaller.

Microparticles having a mean particle diameter of several hundreds nanometers can be obtained by, for example, the method described in Japanese Patent Unexamined Publication No. 2004-99442. Further, microparticles having a mean particle diameter of about 2 to 4 μm can be easily obtained by using a commercially available airflow grinding machine, mechanical grinding machine, or the like. Examples of the commercially available airflow grinding machines include, for example, Ultimizer (registered trademark), jet mills, and the like. By wet grinding using Ultimizer, microparticles having a mean particle diameter of about 4 μm can be obtained, and by dry grinding using a jet mill, microparticles having a mean particle diameter of about 2 μm can be obtained. When dry grinding is carried out by using a jet mill, microparticles having a mean particle diameter of about 4 μm can also be obtained by adjusting nozzle air pressure. Microparticles having a mean particle diameter of about 1 μm can also be easily obtained by variously changing the grinding conditions. Examples of the commercially available mechanical grinding machines include, for example, roll mills, hammer mills, pin mills, sample mills, ball mills, and the like. In general, when dry grinding is performed by using a mechanical grinding machine, a mean particle diameter of 10 μm or 20 μm, for example, can be obtained by variously changing the grinding conditions.

Although it is not intended to be bound by any specific theory, as shown in "Measurement of rate of excretion in feces of medicinally-active ingredient after oral administration of enteric coated capsule to dogs" mentioned in the examples described later, when enteric coated capsules containing a medicinally-active ingredient suspended in a base oil are orally administered to dogs, the rate of excretion in feces becomes less than 50% when the mean particle diameter is 20 μm. It is considered that this is because dissolution rate of the medicinally-active ingredient increases in the gastrointestinal tract when the particle diameter becomes smaller, and moreover, the particles can readily enter into deeper parts of mucosa of the gastrointestinal tract when the particle diameter becomes smaller, thereby retention rate on intestinal wall and in intestinal tract tissues increases, whilst when the particle diameter is large, the medicinally-active ingredient is moved and excreted with the movement of content of the gastrointestinal tract. When a mean particle diameter becomes about 10 μm or smaller, a surprising effect is obtained that the rate of excretion in feces is decreased to the level of 10% or less. The decrease in the rate of excretion in feces means increase in bioavailability. Test results of the following examples clearly demonstrate that an extremely high bioavailability of a hardly water-soluble medicinally-active ingredient can be attained by the pharmaceutical composition of the present invention. The mean particle diameter of the medicinally-active ingredient in the pharmaceutical composition of the present invention can be suitably chosen depending on conditions such as size and structure of internal wall of gastrointestinal tract of a specific animal species, length and structure of gastrointestinal tract, and a type of an active ingredient. For reference, Drug Delivery System 17-4, 321-329 (2002) describes that, when particle diameter becomes smaller, particles enter into deeper parts of mucosa of the gastrointestinal tract, and Pharmaceutical Research, Vol. 18, No. 6, 788-793 (2001) describes that an increase in an amount of adhered particles is observed in rats after the onset of colitis when the particle diameter becomes smaller, whilst in a normal gastrointestinal tract, no difference in amount of particles adhered to mucosa of gastrointestinal tract, is observed as for a particle diameter.

Further, as shown by the results of the comparative test in "Measurement of rate of excretion in feces of medicinally-active ingredient after oral administration of enteric coated capsule to dogs" mentioned in the following examples, when powder (triturated powder) of the medicinally-active ingredient having a mean particle diameter of 1.98 μm and lactose was orally administered to dogs, the rate of excretion in feces was about 60%. Therefore, it is considered that, in the mechanism of action of the decrease in the rate of excretion in feces by the pharmaceutical composition of the present invention, it is important that the microparticles are in an oily suspension state, in addition to that the medicinally-active ingredient is made into microparticles. Although a reason why the rate of excretion in feces is decreased by providing the medicinally-active ingredient microparticles in a state of an oily suspension is not fully elucidated, it is considered that one of the reasons is an increase in dispersibility of the active ingredient in the internal wall of the gastrointestinal tract, attributable to the presence of the base oil. The term "suspension" used herein means a state that the medicinally-active ingredient microparticles are dispersed in a base oil, but not necessarily means a uniform dispersion. It is preferred that the microparticles are uniformly dispersed in a base oil.

A form of the pharmaceutical composition of the present invention are not particularly limited, and may be prepared as a pharmaceutical composition in an arbitrary form, so far that the form is suitable for oral administration and comprises a suspension obtained by suspending the medicinally-active ingredient microparticles in a base oil. A form of capsule is preferred of which inside space can be filled with the suspension and encapsulated. Type of the capsule is not particularly limited, and examples include, for example, soft capsules, microcapsules, seamless soft capsules, seamless microcapsules and the like. A coating such as enteric coating can also be applied to the aforementioned capsules as required.

As the base oil, for example, any of vegetable fats and oils, animal fats and oils and synthetic fats and oils may be used. Specific examples include, for example, as vegetable fats and oils, olive oil, safflower oil, beefsteak plant oil, soybean oil, wheat germ oil, safflower oil, avocado oil, evening primrose oil, sesame oil, and the like, and as animal fats and oils, for example, DHA, EPA, liver oil, yolk oil, seal oil, porcine oil, bovine oil, and the like. Examples of synthetic oils and fats include, for example, medium chain fatty acid triglycerides (Panasate, glyceryl tricaprylate), and the like. A mixture of two or more kinds of base oils may also be used, as required. It is advantageous to choose and use an appropriate base oil from among them depending on type of the medicinally-active ingredient, for example, from a viewpoint of small interactions with the medicinally-active ingredient.

When a suspension is prepared by suspending the medicinally-active ingredient in a base oil, one or two or more kinds of pharmaceutical additives selected from the group consisting of a suspending agent, wax, and a dispersing agent can also be used. Examples of the suspending agent include, for example, glycerin fatty acid esters, sucrose fatty acid esters, white beeswax, hardened oil and the like, examples of the wax include, for example, beeswax, rice wax and the like, and examples of the dispersing agent include, for example, glycerin fatty acid esters, sucrose fatty acid esters, sorbitan fatty acid esters and the like. It is also possible to use wax as a suspending agent, or to use a dispersing agent as a suspending agent, and the purposes of use of the aforementioned pharmaceutical additives are not necessarily limited to those mentioned above. When the aforementioned pharmaceutical additives are used, each of the suspending agent, wax, and dispersing agent may generally be added in an amount within the range of about 0.1 to 10 mass %, preferably 0.2 to 5 mass %, more preferably 0.5 to 2 mass %, based on the total mass of the suspension.

Although an amount of the medicinally-active ingredient contained in the pharmaceutical composition of the present invention is not particularly limited, the amount may be about 1 to 30 mass %, preferably 2 to 25 mass %, more preferably 5 to 20 mass %, based on the total mass of the suspension. Further, although an amount of the base oil in the suspension is not also particularly limited, the amount may be about 70 to 99 mass %, preferably 75 to 98 mass %, further preferably 80 to 95 mass %, based on the total mass of the suspension. Furthermore, it is also possible to add one kind or two or more kinds of other pharmaceutical additives such as emulsifiers, stabilizers, antioxidants, colorants, and aggregation inhibitors, as required. The preparation method of the pharmaceutical composition of the present invention is not particularly limited, and the composition may be readily prepared by a conventional method well known to and widely used by those skilled in the art, for example, by preparing microparticles of a medicinally-active ingredient, then suspending the microparticles in a base oil using an appropriate means, and filling the resulting suspension in capsules.

EXAMPLES

The present invention will be more specifically explained with reference to examples. However, the scope of the present invention is not limited by the following examples.

Example 1

Formation of Microparticles of Medicinally-Active Ingredient

Microparticles of a medicinally-active ingredient having mean particle diameters (median diameters, D50) shown in the following Table 1 were obtained with variously examining the grinding conditions. The mean particle diameters mentioned were calculated from particle diameter distribution measured with a laser diffraction type particle size distribution analyzer LDSA-1400A (Tohnichi Computer Applications Co., Ltd.).

TABLE 1

Grinding conditions and mean particle diameter

| Grinder | Grinding condition | Mean particle diameter |
|---|---|---|
| Jet mill grinder (Seishin Enterprise Co., Ltd.) | Nozzle air pressure: 6 kgf/cm$^2$ | 1.98 μm |
| Jet mill grinder (Seishin Enterprise Co., Ltd.) | Nozzle air pressure: 3 kgf/cm$^2$ | 3.88 μm |
| Sample mill grinder (Nara Machinery Co., Ltd.)) | Screen mesh: 0.5 mm (since clogging was observed in the middle of grinding, it was changed to screen of 0.7 mm) | 9.59 μm |
| Sample mill grinder (Nara Machinery Co., Ltd.)) | Screen mesh: 0.7 mm | 19.76 μm |

The medicinally-active ingredient used in the examples of the specification was a compound of the following formula (i).

[Formula 2]

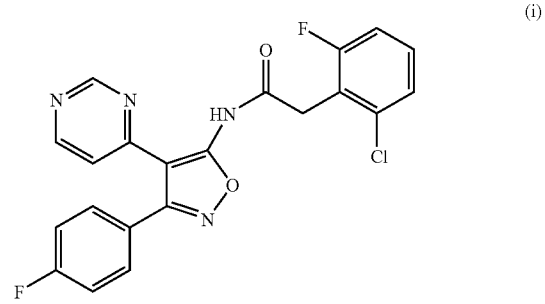

This compound is described in International Publication WO2006/070927, Example 13, and has superior p38MAP kinase inhibitory action, and possibility as an antirheumatic drug, an IBD therapeutic drug and the like are expected. Solubility of this compound is 1.09 μg/mL in Solution 1 (pH 1.2) defined in the Japanese Pharmacopoeia at 37° C., 0.88 μg/mL in Solution 2 (pH 6.8) defined in the Japanese Pharmacopoeia at 37° C., 0.53 μg/mL in a phosphate buffer (pH 7.2) at 37° C., and about 2 mg/mL in Panasate at room temperature.

Examples 2 to 4

Preparation of Enteric Coated Capsules (Mean Particle Diameter of Medicinally-Active Ingredient: 1.98 μm)

To 20 mL of medium chain fatty acid triglycerides (Panasate), 200 mg of glyceryl monostearate and 200 mg of beeswax were added on a water bath at 70° C., and dissolved. The solution was prepared in triplicate.

Three of the solutions were removed from the water bath, the medicinally-active ingredient made into microparticles having a mean particle diameter of 1.98 μm was added to the solutions in amounts of 937.5 mg, 1875 mg, and 3750 mg, respectively, the mixtures were left to cool with stirring until temperature of the mixtures became room temperature, and then dispersion was performed by ultrasonication for 1 minute at room temperature to prepare suspensions having 3 kinds of medicinally-active ingredient concentrations. Each of these suspensions was filled in No. 00 gelatin capsules in a volume of 0.8 mL each, and the capsules were coated with enteric film (HPMCP: hydroxypropylmethylcellulose phthalate, grade: HP-55) by using Doria coater (Powrex). The amounts of contents of the suspensions filled in the enteric coated capsules are shown in Table 2 mentioned below together with those obtained in Examples 5 to 13 described below.

Examples 5 to 7

Preparation of Enteric Coated Capsules (Mean Particle Diameter of Medicinally-Active Ingredient: 3.88 m)

Enteric coated capsules containing suspensions having three kinds of medicinally-active ingredient concentrations shown in Table 2 mentioned below were prepared in the same manner as that in Examples 2 to 4 by using the medicinally-active ingredient made into microparticles having a mean particle diameter of 3.88 μm.

Examples 8 to 10

Preparation of Enteric Coated Capsules (Mean Particle Diameter of Medicinally-Active Ingredient: 9.59 μm)

Enteric coated capsules containing suspensions having three kinds of medicinally-active ingredient concentrations shown in Table 2 mentioned below were prepared in the same manner as that in Examples 2 to 4 by using the medicinally-active ingredient made into microparticles having a mean particle diameter of 9.59 μm.

Examples 11 to 13

Preparation of Enteric Coated Capsules (Mean Particle Diameter of Medicinally-Active Ingredient: 19.76 m)

Enteric coated capsules containing suspensions having three kinds of medicinally-active ingredient concentrations shown in the following Table 2 were prepared in the same manner as that in Examples 2 to 4 by using the medicinally-active ingredient made into microparticles having a mean particle diameter of 19.76 μm.

TABLE 2

Contents of suspensions in enteric coated capsules

| | Example | | |
|---|---|---|---|
| | 2, 5, 8, 11 | 3, 6, 9, 12 | 4, 7, 10, 13 |
| Medicinally-active ingredient (mg) | 937.5 | 1875 | 3750 |
| Glyceryl monostearate (mg) | 200 | 200 | 200 |
| Beeswax (mg) | 200 | 200 | 200 |
| Panasate (mL) | 20 | 20 | 20 |
| Medicinally-active ingredient concentration (mg/mL) | 46.875 | 93.75 | 187.5 |

Examples 14 to 16

Preparation of Seamless Soft Capsules (Mean Particle Diameter of Medicinally-Active Ingredient: 1.98 μm)

Suspensions having three kinds of medicinally-active ingredient concentrations shown in Table 3 mentioned below were prepared in the same manner as that in Examples 2 to 4 by using the medicinally-active ingredient made into microparticles having a mean particle diameter of 1.98 μm. Then, each suspension and a gelatin solution were put into a seamless soft capsule manufacturing machine provided with a double tube nozzle, and capsules were prepared by the dropping-into-liquid method. Coagulated oil was removed from the resulting capsules in a conventional manner, and the capsules were immediately dried in a drum dryer to prepare seamless soft capsules having a diameter of 2.0 mm, a coated film ratio of 30%, and a content per capsule of about 3 μL. The amounts of the contents in the suspension are shown in the following Table 3 together with those obtained in Examples 17 and 18.

Examples 17 and 18

Preparation of Seamless Soft Capsules (Mean Particle Diameter of Medicinally-Active Ingredient: 19.76 μm)

Seamless soft capsules containing suspensions having two kinds of medicinally-active ingredient concentrations shown in the following Table 3 were prepared in the same manner as that in Examples 14 to 16 by using the medicinally-active ingredient made into microparticles having a mean particle diameter of 19.76 μm.

TABLE 3

Contents of suspensions in seamless soft capsules

| | Example | | |
|---|---|---|---|
| | 14, 17 | 15, 18 | 16 |
| Medicinally-active ingredient (g) | 25 | 50 | 100 |
| Glycerol monostearate (g) | 5 | 5 | 5 |
| Beeswax (g) | 5 | 5 | 5 |
| Panasate (mL) | 500 | 500 | 500 |
| Medicinally-active ingredient concentration (mg/mL) | 50 | 100 | 200 |

Example 19

Measurement of Rate of Excretion in Feces of Medicinally-Active Ingredient After Oral Administration of Enteric Coated Capsules to Dogs The enteric coated capsules prepared in Examples 2 to 13 were orally administered in a number of 1 to 4 capsules so as to be a dose of 150 mg of the active ingredient together with 30 mL of purified water to male beagle dogs starved overnight (body weight: 10 to 15 kg, n=3 for each concentration of each particle diameter except for the concentration of 46.9 mg/mL for the medicinally-active ingredient having a mean particle diameter of 19.76 μm, and the concentration of 93.8 mg/mL for the medicinally-active ingredient having a mean particle diameter of 19.76 μm, for which n=5). As a comparative example, triturated powder formed from a mixture of the medicinally-active ingredient having a mean particle diameter of 1.98 μm and lactose (300 mg each was filled into No. 00 capsules, dose of the active ingredient was 150 mg) was similarly administered orally to the dogs.

The dogs were fed 7 hours after the administration, and the animals were allowed to have water ad libitum. Feces up to 24 hours after the administration were collected, made into homogenate, and then added with 0.5 mL of a 0.5 mol/L sodium hydrogencarbonate solution, and the resulting mixture was extracted with 2 mL of diethyl ether. The extract was centrifuged, then the organic layer was dried to hardness at 40° C. under a nitrogen flow, and the residue was dissolved in 0.5 mL of acetonitrile. A potion of the solution in a volume of 10 μL was further dried to hardness at 40° C. under a nitrogen flow. The resulting extraction sample was dissolved in 100 μL of acetonitrile, and the solution was further diluted 10 times, and analyzed by LC/MS/MS (cation ESI method). From the peak areas, amounts of the active ingredient excreted in feces were calculated by using a calibration curve, and rates of excretion of the active ingredient in feces were calculated according to the following equation.

Rate of excretion in feces=(Amount of active ingredient in feces up to 24 hours after administration (mg))/(Amount of active ingredient orally administered)×100 [Equation 1]

The averages of the rates of excretion in feces obtained for the groups are shown in the following Table 4. The results depicted as graphs are shown in FIG. 1.

TABLE 4

Rates of excretion in feces according to particle diameter and concentration in enteric coated capsules

| Mean particle diameter | Concentration of active ingredient (mg/mL) | Rate of excretion in feces (average, %) | Standard deviation |
|---|---|---|---|
| 1.98 μm | 46.9 | 12.27 | 8.64 |
|  | 93.8 | 14.87 | 4.15 |
|  | 187.5 | 22.37 | 13.32 |
| 3.88 μm | 46.9 | 5.46 | 4.18 |
|  | 93.8 | 26.61 | 25.75 |
|  | 187.5 | 35.23 | 9.78 |
| 9.59 μm | 46.9 | 8.88 | 9.48 |
|  | 93.8 | 7.14 | 8.69 |
|  | 187.5 | 22.74 | 9.03 |
| 19.76 μm | 46.9 | 33.46 | 32.98 |
|  | 93.8 | 43.86 | 17.16 |
|  | 187.5 | 47.38 | 23.76 |
| Triturated powder of mixture with lactose | — | 58.13 | 3.00 |

Example 20

Measurement of Rate of Excretion in Feces of Medicinally-Active Ingredient after Oral Administration of Seamless Soft Capsules to Dogs The seamless soft capsules prepared in Examples 14 and 15 mentioned above, namely, seamless soft capsules containing the medicinally-active ingredient having a mean particle diameter of 1.98 μm at concentrations of 50 mg/mL and 100 mg/mL, were orally administered at a dose of 20 mg or 100 mg to dogs (n=3 for each dose at each concentration) in the same manner as that of Example 19, and the rates of excretion in feces of the medicinally-active ingredient were measured. The results are shown in the following Table 5.

TABLE 5

Rates of excretion in feces according to particle diameter and concentration in seamless soft capsules

| Mean particle diameter | Concentration of active ingredient (mg/mL) | Dose (mg/dog) | Rate of excretion in feces (average, %) | Standard deviation |
|---|---|---|---|---|
| 1.98 μm | 50 | 20 | 14.18 | 9.30 |
|  |  | 100 | 6.90 | 5.60 |
|  | 100 | 20 | 26.20 | 2.40 |
|  |  | 100 | 17.10 | 15.50 |

From the above results, it was revealed that even if the active ingredient was hardly water-soluble, the pharmaceutical composition of the present invention gave remarkably lower rates of excretion in feces and higher bioavailability compared with the capsules of the comparative example containing a mixture with lactose.

INDUSTRIAL APPLICABILITY

The pharmaceutical composition of the present invention has enhanced absorption of a medicinally-active ingredient from the intestinal tract and remarkably improved bioavailability. In particular, the composition is useful because extremely high intestinal absorption and bioavailability can be achieved even when the medicinally-active ingredient is hardly water-soluble.

What is claimed is:

1. An oral pharmaceutical composition comprising a suspension of microparticles of 5-[(2-chloro-6-fluorophenyl)acetylamino]-3-(4-fluorophenyl)-4-(4-pyrimidinyl)isoxazole or a salt thereof in a base oil comprising glyceryl monostearate, beeswax, and glyceryl tricaprylate, wherein said microparticles have a mean particle diameter of 10 μm or smaller.

2. The pharmaceutical composition according to claim 1, which contains the 5-[(2-chloro-6-fluorophenyl)acetylamino]-3-(4-fluorophenyl)-4-(4-pyrimidinyl)isoxazole or a salt thereof in an amount within the range of 1 to 30 mass % based on the total mass of the suspension.

3. The pharmaceutical composition according to claim 1, which contains the base oil in an amount within the range of 70 to 99 mass % based on the total mass of the suspension.

4. The pharmaceutical composition according to claim 1, which is used for prophylactic and/or therapeutic treatment of an inflammatory bowel disease.

5. The pharmaceutical composition according to claim 1, which can be obtained by suspending the microparticles of 5-[(2-chloro-6-fluorophenyl)acetylamino]-3-(4-fluorophenyl)-4-(4-pyrimidinyl)isoxazole or a salt thereof having a mean particle diameter of 10 μm or smaller in the base oil.

6. The oral pharmaceutical composition according to claim 1, which is enterically coated.

\* \* \* \* \*